United States Patent
Poston et al.

(10) Patent No.: US 7,425,419 B2
(45) Date of Patent: Sep. 16, 2008

(54) DIAGNOSIS OF PRE-ECLAMPSIA

(75) Inventors: Lucilla Poston, London (GB); Paul Townsend Seed, London (GB); Beverley Jane Hunt, London (GB); Lucy Charlotte Chappell, London (GB)

(73) Assignee: King's College London, London (GB)

( * ) Notice: Subject to any disclaimer, the term of this patent is extended or adjusted under 35 U.S.C. 154(b) by 188 days.

(21) Appl. No.: 10/415,712

(22) PCT Filed: Nov. 2, 2001

(86) PCT No.: PCT/GB01/04892

§ 371 (c)(1),
(2), (4) Date: Sep. 4, 2003

(87) PCT Pub. No.: WO02/37120

PCT Pub. Date: May 10, 2002

(65) Prior Publication Data

US 2004/0038305 A1    Feb. 26, 2004

(30) Foreign Application Priority Data

Nov. 2, 2000    (GB) .................................. 0026823.5

(51) Int. Cl.
*G01N 33/53*    (2006.01)
(52) U.S. Cl. ............................ 435/7.1; 435/4; 436/501; 436/63; 436/86
(58) Field of Classification Search ........................ None
See application file for complete search history.

(56) References Cited

OTHER PUBLICATIONS

Coleman et al. Drug Discovery Today. 2003. 8: 233-235.*
Levine et al. JAMA. 2005. 293: 77-85.*
Reith A et al: "Plasminogen activator inhibitors (PAI-1 and PAI-2) in normal pregnancies, pre-eclampsia and hydatidiform mole." British Journal of Obstetrics and Gynaecology, vol. 100, No. 4, 1993, pp. 370-374, XP008005703, ISSN: 0306-5456.
Estelles A et al: "Changes In The Plasma Levels Of Type 1 And Type 2 Plasminogen Activator Inhibitors In Normal Pregnancy And In Patients With Severe Preeclampsia" Blood, vol. 74, No. 4, 1989, pp. 1332-1338, XP008005702. ISSN: 0006-4971.
Torry D S et al: "Preeclampsia is associated with reduced serum levels of placenta growth factor." American Journal of Obstetrics and Gynecology. Dec. 1998, vol. 179, No. 6 Pt 1, pp. 1539-1544, XP008005713, ISSN: 0002-9378.
Anim-Nyame N et al: "Longitudinal analysis of maternal plasma leptin concentrations during normal pregnancy and pre-eclampsia." Human Reproduction Sep. 2000, vol. 15, No. 9, pp. 2033-2036, XP008005712, ISSN: 0268-1161.
Teppa R J et al: "Free leptin is increased in normal pregnancy and further increased in preeclampsia."Metabolism: Clinical and Experimental. Aug. 2000, vol. 49, No. 8, pp. 1043-1048, XP008005711, ISSN: 0026-0495.

* cited by examiner

*Primary Examiner*—Carla Myers
(74) *Attorney, Agent, or Firm*—Banner & Witcoff, Ltd.

(57) ABSTRACT

The present invention relates to a method of predicting pre-eclampsia (PE). The present invention also relates to a diagnostic kit for performing a method of predicting PE. In particular, the method determining the level of two or more markers selected from placenta growth factor (PlGF), plasminogen activator inhibitor-1 (PAI-1) plasminogen activator inhibitor-2 (PAI-2) and leptin.

19 Claims, 5 Drawing Sheets

DIAGNOSIS OF PRE-ECLAMPSIA

This application claims the benefit of co-pending PCT application PCT/GB01/04892 filed Nov. 2, 2001, which was published under PCT Article 21(2) in English on May 10, 2002(International Publication Number WO 02/37120 A2), which claims the benefit of GB 0026823.5 filed Nov. 2, 2000.

The present invention relates to a method of predicting pre-eclampsia (PE). The present invention also relates to a diagnostic kit for performing a method of predicting PE.

PE is defined according to the guidelines of the International Society for the Study of Hypertension in Pregnancy (Davey et al., Am. J. Obstet Gynecol; 158: 892-98, 1988). Gestational hypertension is defined as two recordings of diastolic blood pressure of 90 mm Hg or higher at least 4 h apart, and severe pressure of 110 mm Hg or higher at least 4 h apart or one recording of diastolic blood pressure of at least 120 mm Hg. Proteinuria is defined as excretion of 300 mg or more in 24 h or two readings of 2+or higher on dipstick analysis of midstream or catheter urine specimens if no 24 h collection was available. Women are classified as previously normotensive or with chronic hypertension before 20 weeks' gestation. For previously normotensive women, PE is defined as gestational hypertension with proteinuria and severe PE as severe gestational hypertension with proteinuria. For women with chronic hypertension, superimposed PE is defined by the new development of proteinuria. PE affects approximately 4% of all pregnancies and is a leading cause of maternal death in the UK. This disease, or the threat of onset, is the commonest cause of elective premature delivery, accounting for approximately 15% of all premature births. The measurement of blood pressure and testing for proteinuria in all pregnant women is carried out predominantly for the detection of PE. These procedures and the care of affected women and of the premature children make considerable demands on healthcare resources. Accurate identification of women at risk could dramatically reduce costs of antenatal care.

Although, there is no widely used treatment for PE (other than premature delivery), we have recently reported a significant reduction in PE in high risk women given supplements of vitamin C and vitamin E (see Chappell et al., The Lancet, 354, 810-816, 1999). Risk was assessed by a test of relatively low sensitivity. More accurate and robust identification of women at risk would target those women most likely to benefit from this, or alternative, prophylactic therapies. Those identified at lower risk could be provided with less intensive and less expensive antenatal care.

There is no widely accepted or accurate method for the early prediction of PE. Elevation of the blood pressure and detection of protein in the urine occur when the disease process is well established, as indicated above. Detection of an abnormality of the blood flow to the uterine artery by Doppler ultrasound in women who later develop PE has been of some predictive use but this abnormality has been found to be relatively non-specific and for this reason has not been adopted in routine clinical practice.

Although some plasma/urine biochemical markers have been shown to be abnormal in the disease process, no single marker has proven to be of adequate sensitivity for use as a predictive indicator. For example the use of placenta growth factor (PlGF) alone as a predictive indicator of PE has been proposed, but the predictive power of this marker could not be determined with any certainty. For example, International patent application WO 98/28006 suggests detecting PlGF alone or in combination with vascular endothelial growth factor (VEGF) in order to predict the development of PE.

Furthermore, the effect of vitamin supplementation on the maternal blood PAI-1/PAI-2 ratio has previously been published by our group (Chappell et al, 1999; Lancet, 354, 810-816) and others have documented raised PAI-1/PAI-2 in established PE (Reith et al, 1993; British Journal of Obstetrics and Gynaecology 100, 370-4) and elevated PAI-1 in women who subsequently developed PE (Halligan et al, 1994; British Journal of Obstetrics and Gynaecology 101, 488-92). PlGF has been shown to be reduced in women with established PE (Torry et al, 1998; American Journal of Obstetrics and Gynaecology 179, 1539-44) and is suggested to be low prior to the onset of the disease. Leptin has been found to increase with gestation in normal pregnant women (Higbman et al, 1998, American Journal of Obstetrics and Gynaecology 178, 1010-5), an observation repeated by ourselves. Leptin has also been shown to rise even ether in established PE, the first report being published by Mise et al., Journal of Endocrinology and Metabolism, 83, 3225-9, 1998. Furthermore, Anim-Nyame et al., Hum. Reprod., 15, 2033-6, 2000, indicates that the elevation of leptin concentrations before PE is clinically evident. This finding is supported by Chappell et al., J. Soc. Gynecol. Invest., 213A, 2001, where it is also indicated that vitamin supplementation reduces plasma leptin in women at risk of PE.

However, none of the prior art documents disclose a reliable, sensitive and specific predictive test for PE.

It has now been found that a combination of markers provide the much needed predictive parameter for the desired early diagnosis of PE.

The present invention provides, a method of specific prediction of pre-eclampsia (PE) comprising determining in a maternal sample the level of two or more markers selected from placenta growth factor (PlGF), plasminogen activator inhibitor-1 (PAI-1), plasminogen activator inhibitor-2 (PAI-2) and leptin.

It has been found that by measuring at least 2 of the markers mentioned above that it is possible to determine with high specificity and sensitivity whether an individual is likely to develop PE. Specificity is defined as the proportion of true negatives (will not develop PE) identified as negatives in the method. Sensitivity is defined as the proportion of true positives (will develop PE) identified as positives in the method. It is preferred that the method comprises measuring 3 of the markers, more preferably all four of the markers.

Preferably, the method of the present invention comprises determining the level of placenta growth factor (PlGF) with the level of one of the following:

(i) plasminogen activator inhibitor-2 (PAI-2);
(ii) the ratio of plasminogen activator inhibitor-1 (PAI-1) to plasminogen activator inhibitor-2 (PAI-2); and
(iii) leptin.

It has been found that these specific combinations are particularly useful for determining whether an individual is likely to develop PE.

The term "pre-eclampsia" as used herein is defined according to the guidelines of the International Society for the Study of Hypertension in Pregnancy, as described above.

The term "specific prediction of pre-eclampsia" as used herein means that the method of the present invention is used to specifically predict the development of PE. In particular, the method of the present invention enables one to determine whether an individual is likely to develop PE.

The maternal sample is taken from a pregnant woman and can be any sample from which it is possible to measure the markers mentioned above. Preferably the sample is blood. The samples can be taken at any time from about 10 weeks gestation. Preferably the sample is taken at between 12 and 38 weeks gestation, more preferably the samples are taken between 20 and 36 weeks.

The term "placenta growth factor" (PlGF) refers to the free form found in the individual. The amino acid sequence human PlGF is known (see NCBI Protein database, accession no. XP 040405). There are numerous methods of detecting PlGF including the commercially available Quantikine Human PlGF immunoassay from R&D Systems Inc.

The term "plasminogen activator inhibitor-1" (PAI-1) is a standard term used in the art and is clear to those skilled in the art. In particular, the sequence of the human form of PAI-1 is given in the NCBI Protein database under accession no. AAA 60003. There are numerous methods of detecting PAI-2 including the commercially available Tint Elize PAI-1 kit from Biopool International.

The term "plasminogen activator inhibitor-2" (PAI-2) is a standard term used in the art and is clear to those skilled in the art. In particular, the sequence of the human form of PAI-2 is given in the NCBI Protein database under accession no. CAA 02099. There are numerous methods of detecting PAI-2 including the commercially available Tint Elize PAI-2 kit from Biopool International.

The term "leptin" is a standard term well known to those skilled in the art. In particular, the amino acid sequence of a human form of leptin is given in the NCB 1 Protein database under accession no. P41159. There are numerous methods of detecting leptin, for example, the Quantikine, human leptin immunoassay from R&D Systems Inc.

In a particularly preferred embodiment of the present invention, the method of the present invention is performed by determining the level of two or more of the markers using the automatic DELFIA® system which is available from Wallac, Finland. Automatic DELFIA® is an automated system specifically designed and optimised for performing immunoassays and can therefore be used to measure the levels of two or more of the markers used in the method of the present invention. The automatic DELFIA® systems measures the concentration of the markers using fluorescence and all four markers can be detected in a single well/sample.

We obtained samples of blood from pregnant women who were considered at risk of PE on the basis of the uterine artery Doppler test or because they had had the disease in a previous pregnancy. Blood samples were obtained from 20 weeks of pregnancy at intervals of 4 weeks until delivery. We measured a selection of biochemical markers implicated in PE, including vitamin C, homocysteine, plasma lipids and 8-epi prostaglandin $F_{2\alpha}$ but none proved to be effective in prediction. We found that the ratio of plasminogen activator inhibitor −1 (PAI-1) and PAI-2 increased prior to the onset of the disease, whereas placenta growth factor (PlGF) failed to show the pronounced rise normally observed in healthy pregnancies. Plasma leptin normally rises in pregnancy but we found that it increased to a much greater extent in women destined to develop PE. Combinations of these markers (see below) proved to be excellent in the sensitive and specific prediction of subsequent PE.

In testing the combinations described above it has been found that for patients who will develop PE (i.e. the prediction is positive) there is no increase in the level of PlGF with gestation whereas PlGF normally increases with gestation. If the combination of markers PlGF and PAI-2 is used, a positive prediction is given by the combined levels of PlGF and PAI-2 being less than normal.

Where the combination of markers PlGF and the ratio of PAI-1 to PAI-2 is used, a positive prediction is given by a combination of a reduced level of PlGF and the ratio of PAI-1 to PAI-2 being greater than normal.

If the combination of the markers PlGF and leptin is used, a positive prediction is given by the ratio of leptin to PlGF being greater than normal.

In order to determine whether the level or ratio of the markers referred to above is greater than or less than normal, the normal level or ratio of the relevant population needs to be determined. The relevant population may be defined based on, for example, ethnic background or any other characteristic that may affect normal levels of the markers. The relevant population for establishing the normal level or ratio of the markers is preferably selected on the basis of low risk for PE (i.e. no known risk marker for PE, such as previous PE, diabetes, prior hypertension etc.). Once the normal levels are known, the measured levels can be compared and the significance of the difference determined using standard statistical methods. If there is a statistically significant difference between the measured level and the normal level, then there is a significant risk that the individual from whom the levels have been measured will develop PE.

In a preferred embodiment of the present invention, the markers PlGF and PAI-2 may be combined using the algorithm:

$$d(\log_e[\text{PAI-2}]) + (\log_e[\text{PlGF}])$$

wherein d is a constant in the range of about 0.03 to 48.6. Preferably d is in the range of 0.072 to 7.6, more preferably in the range of 0.0336 to 2.2. Most preferably d is 0.75 or 1. Alternatively markers PlGF and PAI-2 may be combined using the algorithm:

$$[\text{PAI-2}]^{d}*[\text{PlGF}]$$

wherein d is as defined above. The sign "*" is used as the sign for multiplication.

In a particularly preferred embodiment, d is 1 and the previous algorithm can be written as [PAI-2]*[PlGF]. Using this algorithm, and assuming the concentration of PAI-2 is measured as ng/ml and the concentration of PlGF is measure as pg/ml, it has been found that if the value obtained using the algorithm is <35,000 that the sensitivity and specificity of predicting PE is 67% and 100%, respectively. If the value obtained using the algorithm is <50,000 that the sensitivity and specificity of predicting PE is 80% and 34%, respectively (see Table 10 below).

In a further preferred embodiment of the present invention, the markers PlGF and the ratio of PAI-1/PAI-2 may be combined using the algorithm:

$$(\log_e[\text{PlGF}]) - (g*\{\text{PAI-1/PAI-2 ratio}\})$$

wherein g is a constant in the range of about −19.4 to 3.6. Preferably g is in the range of 0.655 to 15.5, more preferably 1.37 to 7.0. In a particularly preferred embodiment g is 3.0. Using the algorithm when g is 3.0, and assuming the concentration of PlGF is measured as pg/ml, it has been found that if the value obtained using the algorithm is <4.5 that the sensitivity and specificity of predicting PE is 53% and 100%, respectively. If the value obtained using the algorithm is <5 the sensitivity and specificity of predicting PE is 80% and 88%, respectively (see Table 4 below).

It has also been found that by measuring the leptin/PlGF ratio, when the leptin concentration is in ng/ml and PlGF concentration is pg/ml, a value of >0.1 provides a method of predicting PE with 67% sensitivity and 100% specificity. When the value is >0.05, the method of predicting PE has 80% sensitivity and 88% specificity.

It can be seen that the level of sensitivity and specificity can be altered by altering the threshold level. In some situations, e.g., when screening large numbers of women at low risk of PE, it is important to have high specificity. In other situations, it may be important to have a balance between high sensitivity and specificity, e.g., when considering individual women at high risk of PE a balance between high sensitivity and specificity is needed.

The present invention offers many benefits. In addition to facilitating accurate targeting of interventions e.g. vitamin supplements, considerable saving on health care resources can be expected due to stratification of antenatal care and reduced neonatal special care costs. In the research and development area, identification of high risk patients will greatly facilitate future clinical trials. At present due to inadequate methods of prediction, large numbers of pregnant women unnecessarily receive interventions in clinical trials.

The method the present invention may be performed in conjunction with other tests for diagnostic indicators, such as blood pressure, level of uric acid etc.

The method of the present invention may also be used in order to monitor the efficiency of a prophylactic treatment for preventing the development of PE, wherein a reduction in the risk of developing PE will be indicative of the prophylactic treatment working.

More than twenty biochemical markers have been shown previously to be associated with established PE and there would be no logical prior reason for choosing PAI-1, PAI-2, PlGF and leptin in any prospective longitudinal study for assessment of use as predictive indicators. Moreover very few groups have evaluated any individual marker prospectively in the same women from whom samples were taken at intervals throughout their pregnancy. Importantly none has measured the different markers in the same women, unlike in the present application.

Once a value has been obtained using one of the algorithms mentioned above, the log-odds of the individual developing PE can be calculated using the formula:

$$y = a + bx$$

wherein y is the log-odds of the individual developing PE, x is the value obtained using one of the algorithms and a and b are constants (values provided later) derived from logistic regression analysis of our previously acquired data set adjusted on the assumption of 4% prevalence of PE in the population. This approach, known as logistic regression, is widely used in clinical research.

In order to demonstrate how the formula can be used to determine log-odds of an individual developing PE, the following information demonstrates how it is possible to determine the desired values of a and b so that a log-odds value can be obtained having any desired confidence interval (CI).

The following prediction formulae are calculated based on the sample of pre-eclamptics and controls analysed at 24 weeks. The formulae give the log-odds of PE for any given value of the predictor. The probability is just exp(log-odds)/(1+exp(log-odds)) (exp means the inverse function of the natural logarithm).

All values are given corrected for a prevalence of 4%, log-odds of 4% =log(4/96) =−3.18. To convert to a different prevalence, say 20%, first work out the new log-odds =log(20/80)=−1.39. The difference is −3.18−(−1.39)=1.79

The value of the constant "a" must be increased by this amount. The value of "b" is unchanged.

The best values of "a" for use with algorithm log, [PlGF]−3*(PAI-1/PAI-2), giving the highest CI is 23.042. However, the value for "a" with a CI of 75%, 95% or 99% is:
75% limits: 9.314 to 36.771
95% limits: −0.348 to 46.432
99% limits: −7.697 to 53.782

The best value of "b" for use with algorithm $\log_e$[PlGF]−3*(PAI-1/PAI-2), giving the highest CI is −5.223. However, the value for "b" with a CI of 75%, 95% or 99% is:
75% limits: −7.940 to −5.620
95% limits: −9.852 to −3.708
99% limits: −11.306 to −2.254

The best value of "a" for use with the algorithm leptin/PlGF ratio is −5.801. However, the value of "a" with a CI of 75%, 95% or 99% is:
75% limits: −6.895 to −4.707
95% limits: −7.665 to −3.937
99% limits: −8.251 to −3.351

The best value of "b" for use with the algorithm leptin/PlGF ratio is 42.197. However, the value of "b" with a CI of 75%, 95% or 99% is:
75% limits: 22.393 to 58.948
95% limits: 8.455 to 72.886
99% limits: −2.147 to 83.489

The best value of "a" for use with the algorithm [PAI-2]*[PlGF] is −0.919. However, the value of "a" with a CI of 75%, 95% or 99% is:
75% limits: −1.923 to 0.084
95% limits: −2.630 to 0.791
99% limits: −3.167 to 1.328

The best value of "b" for use with the algorithm [PAI-2]*[PlGF] is 0.000. However, the value of "b" with a CI of 75%, 95% or 99% is:
75% limits: −0.000 to −3.114
95% limits: −0.000 to −3.114
99% limits: −0.000 to −3.114

It is therefore possible for those skilled in the art to determine the log-odds of a patient developing PE with any desired CI based on the information given herein and by using standard statistical analysis.

The present invention also provides a diagnostic kit for performing the method of the present invention. The kit comprises reagents required to determine the level of the markers being measured. Suitable agents for assaying for the markers include enzyme linked immunoassay reagents, RIA reagents and reagents for Western blotting.

The present invention is now described by way of example only, with reference to the following figures.

EXAMPLES

Example 1

The method of the present invention is preferably carried out at the 20th week of pregnancy or later e.g. at 24 weeks.

Briefly, the method of the present invention is performed by taking 5 mls of venous blood from a pregnant woman into a vacutainer with either trisodium citrate or 0.5M EDTA as anticoagulant. The plasma is decanted after centrifugation and stored at −20° C. until assay. Use may be made of commercially available assays such as the following: Assays for leptin (Quantikine, Human Leptin immunoassay, immunoassay R& D systems Inc, Minneapolis Minn. 55413,USA); PlGF (Quantikine Human PlGF immunoassay R& D systems Inc, as above); PAI-1 (TintElize PAI-1, Biopool International, Umea,Sweden or Ventura Calif. 93003, USA) and PAI-2 (TintElize PAI-2, Biopool International, as above). The assays are performed according to the manufacturer's instructions. The following are calculated from the plasma concentrations obtained in the assays:
1. $(\log_e[PlGF])-(3.0*PAI-1/PAI-2\ \text{ratio})$
2. $0.75(\log_e[PAI-2])+(\log_e[PlGF])$
3. leptin/PlGF The number calculated in 1, 2 or 3 (referred to below as "x") is then entered on specially designed software (provided) in the equation $$y=a+b\,x$$

where y is the calculated log-odds of the patient developing PE and a and b are constants (values provided later) derived from logistic regression analysis of our data set adjusted on the assumption of 4% prevalence of PE in the population and x is the calculated value from 1, 2 or 3. This approach, known as logistic regression, is widely used in clinical research. We claim novelty for establishing appropriate values for a and b in this context.

The probability (0-100%) of developing PE for each of the three tests is given by $\exp[y/(1+y)]*100\%$. This value can be adjusted for population prevalence of PE or by risk for an individual patient.

The method of testing for prediction of PE involves the simultaneous measurement of PAI-1, PAI-2, PlGF and leptin in 'kit' form. Each assay is currently based on a calorimetric test e.g. an enzyme linked immunoabsorbent assay, ELISA, in which intensity of colour development in a test 'well' is proportional to the concentration of marker present. The kit involves four wells, one specific for each marker and the tester (hospital biochemist) adds a known volume of the pregnant woman's blood plasma to each well. The colours are then assessed simultaneously on a colour density scanner. These scanners are available in all routine hospital laboratories. The result for each marker (obtained on the print out from the scanner) is then typed into a specially designed computer program. For each of the algorithms described above the program computes a single value. This value can be compared to the limits of the normal range provided in Table 4 below.

Depending on this value, the woman's % risk (0-100%) is assessed and determined.

As indicated previously, it is particularly preferred that the method of the present invention is performed using the automatic DELFIA® system.

Algorithm Development

In devising algorithms for the combination of the specified markers, the best value was obtained using $(\log_e[PlGF])-(3.0*\{PAI-1\ /PAI-2\ \text{ratio}\})$. At 24 weeks gestation, the area under the ROC curve was 0.96 (95% CI 0.88-1.99). A perfect test would give an area of 1 whilst a test no better than chance would give an area of 0.5. This formula also worked well for samples tested at earlier and later weeks of gestation, although to be of clinical use the earlier the risk can be assessed, the more useful will be the test. Areas under the curve at the different gestations tested are given below in Table 1 and shown graphically for 24 weeks gestation in the FIG. 1.

TABLE 1

| Gestation | ROC area | 95% CI |
| --- | --- | --- |
| 20 weeks | 0.81 | 0.63-0.98 |
| 24 weeks | 0.96 | 0.88-1.00 |
| 28 weeks | 0.91 | 0.78-1.00 |
| 32 weeks | 0.96 | 0.90-1.00 |
| 36 weeks | 0.99 | 0.97-1.00 |

We have also found that combination of PAI-2 and PlGF gives an almost equally good prediction of risk using the algorithm $0.75(\log_e[PAI-2])+(\log_e[PlGF])$. See Table 2.

TABLE 2

| Gestation | ROC area under curve | 95% confidence interval |
| --- | --- | --- |
| 20 weeks | 0.80 | 0.60-1.00 |
| 24 weeks | 0.88 | 0.74-1.00 |
| 28 weeks | 0.91 | 0.77-1.00 |
| 32 weeks | 0.94 | 0.86-1.00 |
| 36 weeks | 0.97 | 0.91-1.00 |

Additionally we found that a combination the ratio of Leptin/PlGF is a good predictive indicator of PE (see Table 3).

TABLE 3

| Gestation | ROC area under curve | 95% confidence interval |
| --- | --- | --- |
| 20 weeks | 0.78 | 0.59-0.98 |
| 24 weeks | 0.87 | 0.74-1.00 |
| 28 weeks | 0.80 | 0.60-1.00 |
| 32 weeks | 0.96 | 0.90-1.00 |
| 36 weeks | 0.90 | 0.75-1.00 |

An additional value of these prediction tests lies in their poor predictive value for the later development of growth retardation. Several markers, particularly those synthesized in placental tissue, are similarly raised in PE and in pregnancies associated with fetal growth retardation but uncomplicated by PE. Neither of the combinations of markers we have used were predictive of growth retardation i.e. they are specific for PE.

The following Tables show typical values of the markers and marker ratios and values obtained from the corresponding algorithms given above.

TABLE 4

Normal Ranges in healthy women with normal pregnancy outcomes.

| Marker | Median | Normal Range (90% Reference Range) |
|---|---|---|
| PlGF pg/ml | 586 | 292 to 1177 |
| PAI-1 ng/ml | 40.0 | 25.4 to 63.0 |
| PAI-2 ng/ml | 169 | 78 to 363 |
| PAI-1/PAI-2 | 0.24 | 0.10 to 0.55 |
| Leptin ng/ml | 18.7 | 8.4 to 42.0 |
| Log ePlGF-(3.0× {PAI-1/PAI-2} ratio | 5.57 | 4.71 to 6.43 |
| Leptin/PlGF | 0.030 | 0.013 to 0.069 |
| 0.75(logPAI-2) + (logPlGF) | 10.20 | 9.30 to 11.00 |

TABLE 5

PE-ranges in high risk women who later develop PE

| Marker | Median | Normal Range (90% Reference Range) |
|---|---|---|
| PlGF pg/ml | 221 | 54 to 910 |
| PAI-1 ng/ml | 39.8 | 23.5 to 67.5 |
| PAI-2 ng/ml | 103.0 | 49.4 to 214.6 |
| PAI-1/PAI-2 | 0.387 | 0.180 to 0.830 |
| Leptin ng/ml | 30.7 | 14.9 to 63.2 |
| $\log_e$PlGF-(3.0× {PAI-1/PAI-2} ratio | 4.01 | 2.36 to 5.67 |
| Leptin/PlGF | 0.124 | 0.020 to 0.764 |
| 0.75($\log_e$PAI-2) + ($\log_e$PlGF) | 8.80 | 7.20 to 10.40 |

TABLE 6

Values for a and b in algorithms 1 to 3.

| Equation | a | b |
|---|---|---|
| $\log_e$PlGF-(3.0× {PAI-1/PAI-2} ratio | 28.1 | -5.65 |
| Leptin/PlGF | 6.56 | 2.31 |
| 0.75($\log_e$PAI-2) + ($\log_e$PlGF) | 24.9 | 2.62 |

Figure 7:
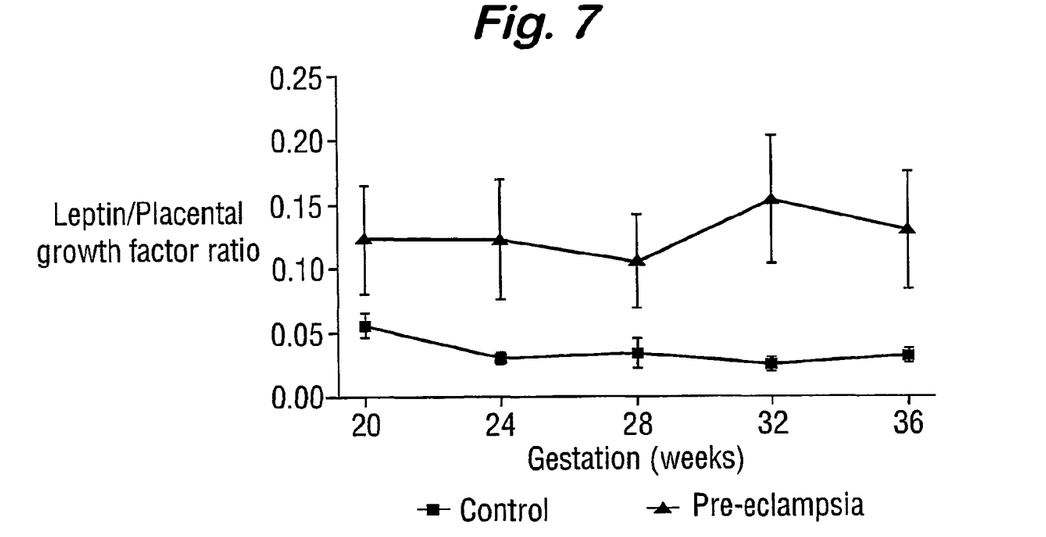
FIG. 7 shows the level of Leptin/PlGF ratio variation during the gestation period.
Figure 8:
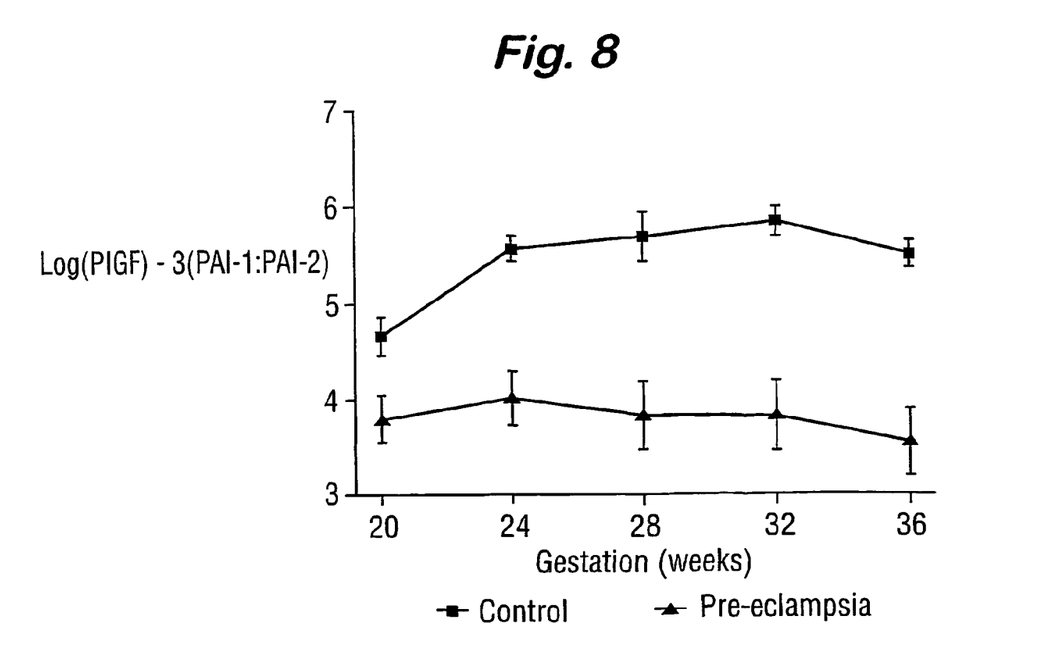
FIG. 8 shows the level of $(\log_e[PlGF])-(3.0*\{PAI-1/PAI-2\ \text{ratio}\})$ variation during the gestation period.
Figure 9:
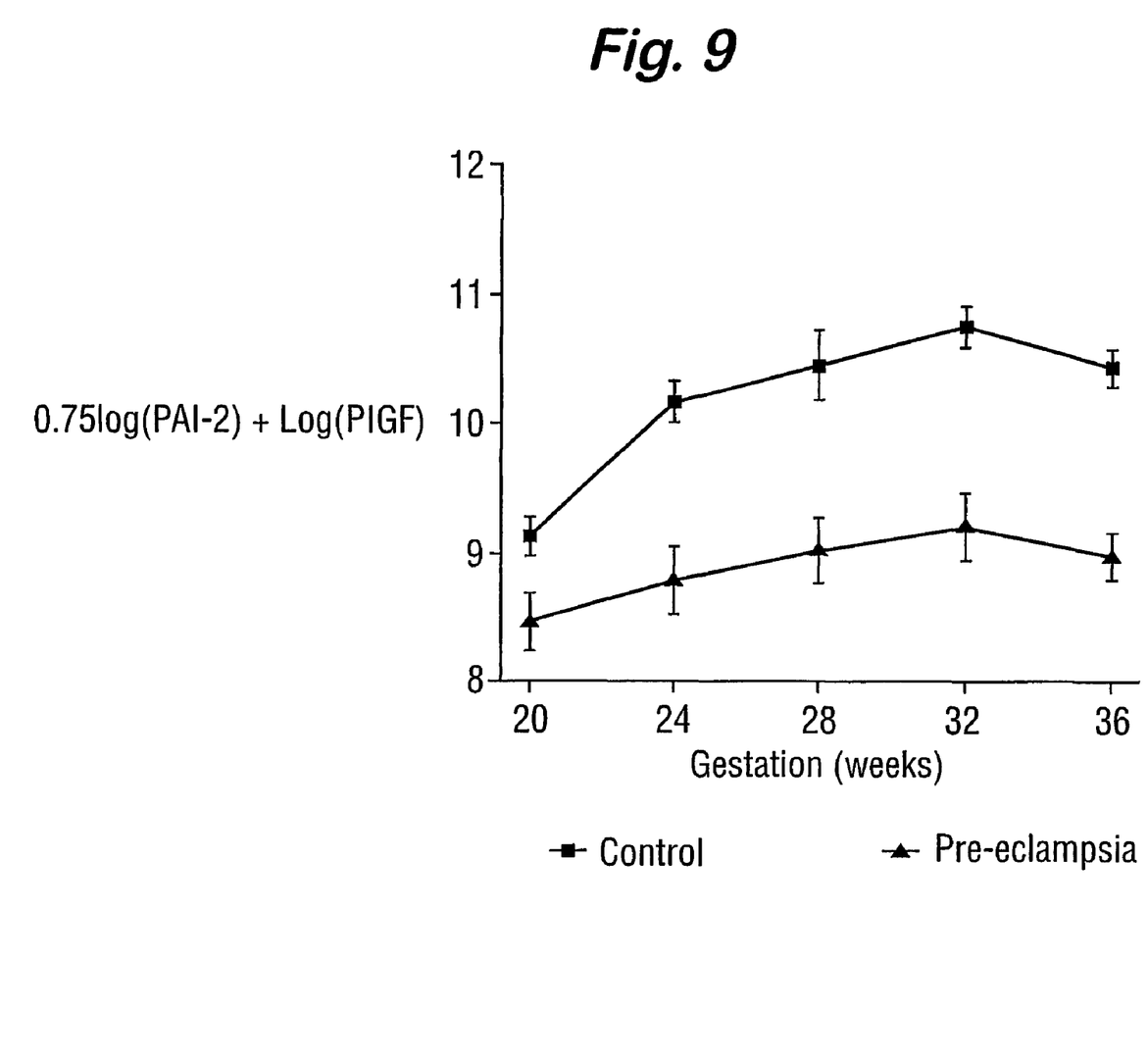
FIG. 9 shows the level of $(\log_e[PAI-2])+(\log_e[PlGF])$ variation during the gestation period.

The variation in the ratio of leptin to PlGF for controls and women who later developed PE is shown in FIG. 7. The variation in PlGF and PAI-1/PAI-2 ratio as determined using algorithm $\log_e$[PlGF]−3*(PAI-1/PAI-2) for controls and women who later developed PE is shown in FIG. 8. The variation in PAI-2 and PlGF levels as determined using algorithm 0.75 ($\log_e$[PAI-2])+$\log_e$[PlGF] for controls and women who later developed PE is shown in FIG. 9.

Example 2

Methods

Subjects. Subjects were recruited with local ethical committee approval from St Thomas' Hospital and Chelsea and Westminster Hospital, London, UK.

High risk women were identified by PE requiring delivery before 37 weeks' gestation in the preceding pregnancy or by abnormal uterine artery Doppler FVW (defined as a resistance index ≧95 1 centile for gestation or the presence of an early diastolic notch). The study group were drawn from the placebo arm of a randomized clinical trial of antioxidant supplementation. 1512 women were screened at 18-22 weeks and at 24 weeks gestation for persistent abnormalities of the Doppler FVW. A total of 160 women participated in the clinical trial of antioxidants until delivery. Of the 81 high-risk women reported in the present study from the placebo arm, 60 women entered the study on the basis of abnormal Doppler FVW and 21 on the basis of PE in the previous pregnancy. The 81 women were followed longitudinally with blood sampling at 4 weekly intervals. Data from the women who developed either PE with or without SGA (PE, n=21) or who delivered small for gestational age (SGA, n=17) infants without PE are reported. Of the women who developed PE, six had essential hypertension (five were taking methydopa at the time of recruitment) and one had antiphospholipid syndrome. Five women were taking aspirin; this was not an exclusion criterion for the trial. Gestational Pre-eclampsia is defined by the International Society for the Study of Hypertension in Pregnancy guidelines (Am. J. Obstet Gynecol., 158: 892-98, 1988), which describes PE as gestational hypertension with superimposed PE. Gestational hypertension was defined as two recordings of diastolic blood pressure ≧90 mmHg ≧4 hours apart and severe gestational hypertension as two recordings of diastolic blood pressure ≧110 mmHg ≧4 hours apart or one recording of diastolic blood pressure ≧120 mmHg. Proteinuria was defined as ≧300 mg/24 hrs or two readings of ≧2+on dipstick analysis of mid-stream or catheter urine specimens if no 24 hour collection was available. SGA infants were defined as those ≦10th centile for gestation and gender, corrected for maternal height, weight, parity and ethnicity using centile charts (Lancet et al., 339: 283-287, 1992).

Low risk women All women attending the hospital antenatal clinics for routine care during the trial recruitment period who consented to the study and who, on screening, had a normal Doppler FVW and no other co-existing disease or risk markers were invited to participate. 33 consented and 1 failed to finish the study; data are presented from the 27 women who delivered infants of appropriate size for gestational age (AGA). Since SGA infants delivered by low risk women (with normal uterine artery Doppler FVW) are more likely to be 'normally' small than to be growth restricted, pregnancies associated with SGA in this group were not included in the SGA group.

Blood sampling. Venous blood was drawn from an uncuffed arm into tubes with appropriate additions for each of the factors (also referred to herein as markers) assayed. Samples were placed immediately on ice and centrifuged within 3 hrs. Supernatants were stored at −70° C. prior to assay.

Analysis of Biochemical Markers

Indices of Antioxidant Status and Oxidative Stress

Samples for assay of ascorbic acid and α tocopherol were stored in 2% metaphosphoric acid. Ascorbic acid and uric acid were determined by reverse phase high pressure liquid chromatography (HPLC) (Pediatr Res et al., 36: 487-93, 1994) (ascorbic acid; lower limit of detection 5nM; intra-assay coefficient of variation [CV] 2.2%; inter-assay CV 3.5%; uric acid; lower limit of detection 5nM; intra-assay CV 2.6%, inter-assay CV 3.8%). α-tocopherol was assayed by reverse phase HPLC (Br. J. Nutr et al., 63: 631-8, 1990) (lower limit of detection 10nM; intra-assay CV 2.1%; inter-assay CV 3.9%). Due to sample losses of methodological origin the isoprostane 8-epi-PGF$_{2\alpha}$(a marker of lipid peroxidation) was not determined in all women, but was assessed in available samples from 21 low risk, 13 SGA and 17 pre-eclamptic women as previously described (J Chromatogr B.

Biomedical Applications., 667: 199-208, 1995), by gas chromatography-mass spectrometry. Previous studies from our laboratory indicated that these numbers would provide adequate power to reveal significant differences between groups.

Indices of placental insufficiency Plasminogen activator inhibitor (PAI-2) was determined by ELISA (Tintelize, Biopool International, Sweden; lower limit of detection 6 ng/ml; intra-assay CV 3.7%; inter-assay CV 3.0%). Serum leptin was evaluated by RIA using $^{125}$labelled human leptin (LINCO Research, Inc, Missouri, USA; lower limit of detection 0.5 ng/ml; intra assay CV 4.5%; inter-assay CV 4.9%). PlGF was evaluated by ELISA (R&D systems, Abingdon, UK; lower limit of detection 7 pg/ml; intra assay CV 5.6%-7.0%; inter-assay CV 10.9%-11.8%).

Index of endothelial function. Plasminogen activator inhibitor-1 (PAI-1) was determined by ELISA (Tintelize, Biopool International, Sweden; lower limit of detection 0.5 ng/ml; intra-assay CV 3.3%; inter-assay CV 2.9%).

Lipids Serum triglycerides and total cholesterol were measured by enzymatic colorimetric tests (UNIMATE 5 TRIG and UNIMATE 5 CHOL respectively, Roche/BCl, Lewes, Sussex, UK). HDL-cholesterol was determined by detergent based isolation and enzyme linked colorimetric detection (DIRECT HDL CHOLESTEROL, Randox laboratories, Co Antrim, Northern Ireland). LDL-cholesterol was estimated by calculation from triglycerides and HDL cholesterol. Apo A-1 and Apo B were evaluated by immunoturbidimetry (Dade/Behring, Milton Keynes, UK).

Statistical Analysis

Data were analysed in Stata 6.0 (StataCorp, College Station, Tex.). Summary scores (mean of 2 or more measurements made in weeks 20-36) were calculated for each biochemical marker (Matthews et al., Br Med. J., 300: 230-5, 1990). Log transformations & geometric means were used for 8-epi-PGF$_{2\alpha}$, leptin, PAI-1, PAI-2, PAI-1/PAI-2 ratio, triglycerides, vitamin E/cholesterol ratio and uric acid. As PAI-1 changed considerably with gestation, a 2-way interaction between time and outcome were fitted with Generalised Estimating Equations (GEE). (Biometrika et al., 73: 13-22, 1986) GEE was also used to estimate the impact of race (Caucasian/European vs. African/Caribbean) and parity.

Markers showing significant differences (8-epi PlGF2α, HDL Cholesterol, Uric acid, PAI-1/PAI-2 ratio, leptin and PlGF) were considered as possible predictors of PE at 20 and 24 weeks. Areas derived from Receiver Operation Characteristic (ROC) curves were used to assess their usefulness. Multiple logistic regression was use to develop three combined predictive indices (details available on request). Sensitivity and specificity were calculated for appropriate cut-points. A smoothed ROC curve (Stata Technical Bulletin., 2000; 52: sg120) is given for the best index.

Percentage differences from the reference group are given with 95% confidence intervals (CI) using robust standard errors (Biometrika et al., 73: 57-64, 1988). Significance at the 5% level is claimed when the CI excludes no effect (0% or ROC area 0.5).

Results

Study entry details are given in Table 7 and perinatal characteristics in Table 8. There were 45% (95% CI 21 to 69%) more women of African or Caribbean origin in the PE group than in the low risk group; no other differences were significant.

Longitudinal Profile of Biochemical Markers

Some women delivered before the last (36 week) sample. There were a few additional omissions due to failure to attend the clinic and loss of samples for methodological reasons. Biochemical markers other than 8-epi-PGF$_{2\alpha}$(as detailed above) were measured on at least four occasions for the majority of women (66%-84%, mean 78% of women; depending on marker).

Indices of antioxidant status and oxidative stress Plasma ascorbic acid concentrations were decreased in both the SGA (−39%; CI −61% to −17%) and PE groups (−30%; CI −50% to −11%) compared to low risk women. Differences between SGA and PE groups were not significant. Plasma α-tocopherol concentrations corrected for cholesterol showed a small rise over gestation in the low risk women, but no significant differences were observed between groups. Summary scores for plasma 8-epi-PGF$_{2\alpha}$concentrations showed a trend towards higher values in the PE group (mean difference 51%; CI −1% to 131%) compared to the low risk women. A less pronounced trend was also observed in the SGA group (−41%; CI −6% to 114%). Uric acid concentrations increased with gestation in all groups but the rise in the PE group was greater than in low risk women (21%; CI 8% to 36%) or in the SGA group (difference 19%, CI 4% to 37%).

Figure 2:
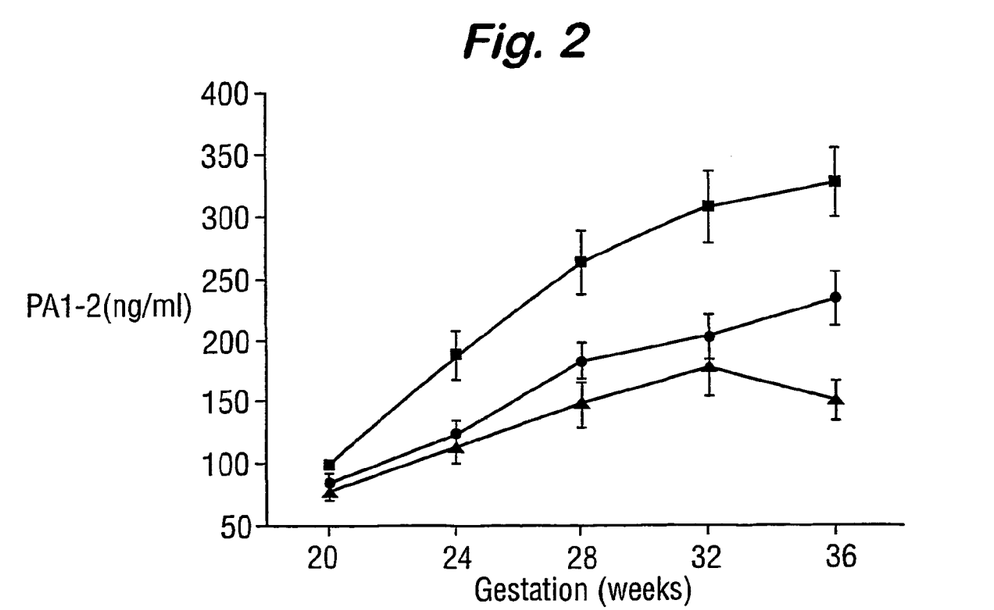
FIG. 2 shows the level of PAI-2 variation during the gestation period, wherein(■) is low risk women, (▲) is women who subsequently developed PE, and (●) is women who did not develop PE but delivered small for gestational age (SGA) infants.
Figure 3:
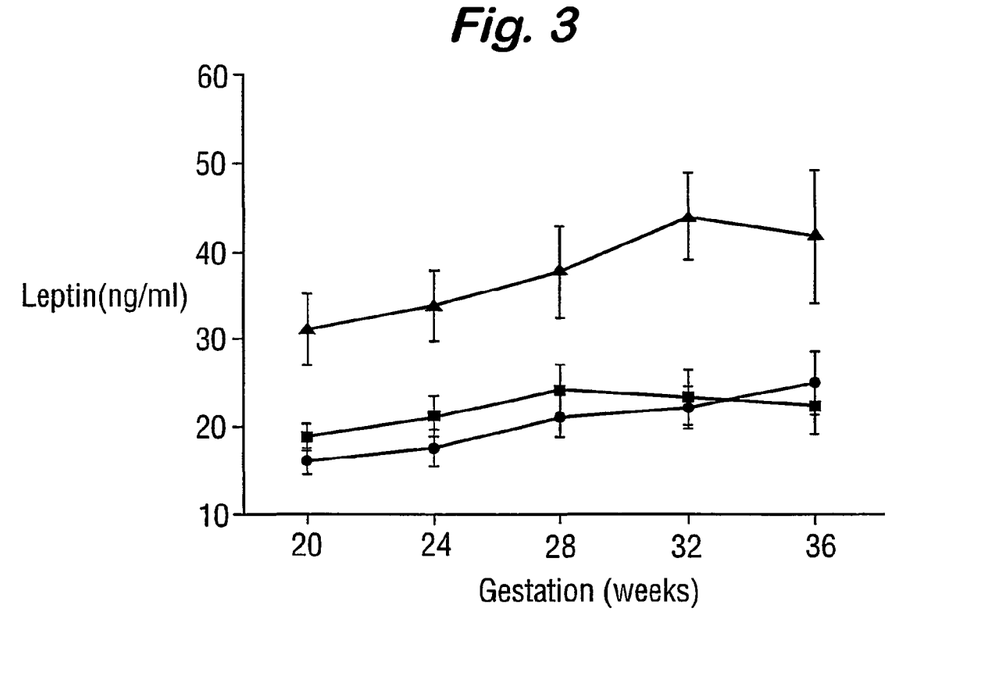
FIG. 3 shows the level of Leptin variation during the gestation period, wherein (■) is low risk women, (▲) is women who subsequently developed PE, and (●) is women who did not develop PE but delivered small for gestational age (SGA) infants.
Figure 4:
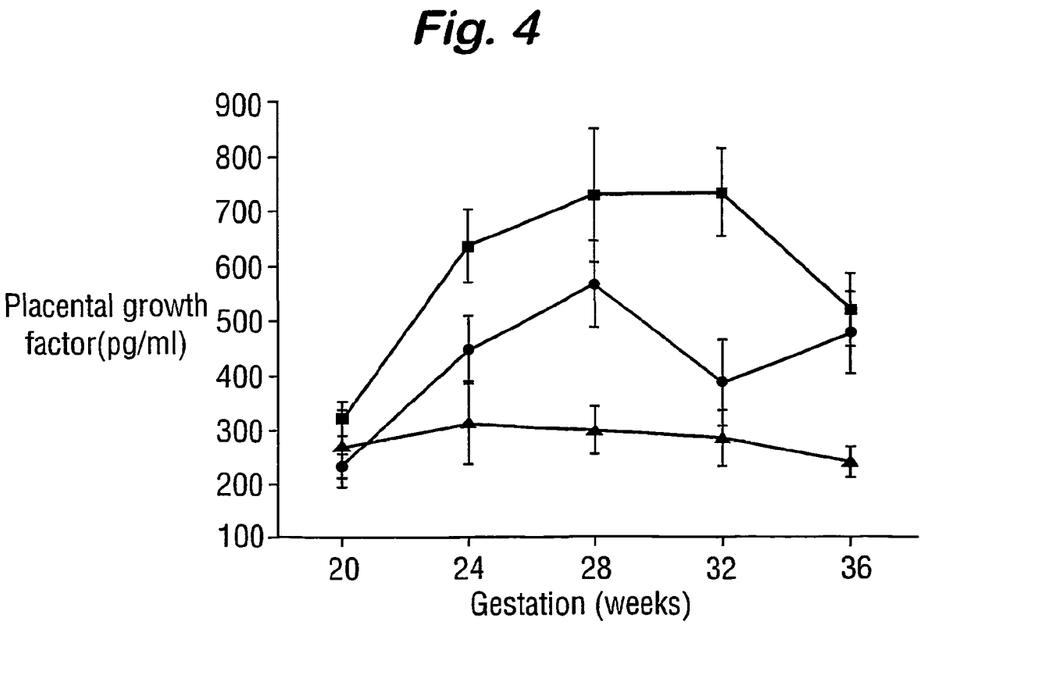
FIG. 4 shows the level of PlGF variation during the gestation period, wherein (■) is low risk women, (▲) is women who subsequently developed PE, and (●) is women who did not develop PE but delivered small for gestational age (SGA) infants.

Indices of placental insufficiency. Compared with low risk women, the PAI-2 concentration was lower in both the SGA (−28%; CI −41% to −11%) and PE groups (−43%; CI −55% to −26%) but the difference between the latter groups was not significant (see FIG. 2). The serum leptin concentration was significantly higher in the PE group compared with SGA (92%; CI 39% to 165%) or low risk groups (74%, CI 21% to 135%) and values in the SGA and low-risk groups were similar (see FIG. 3). These differences remained significant after correction for BMI. PlGF in the low risk women rose and then fell with gestational age (see FIG. 4). This profile was blunted in the SGA group (−35%; CI −57% to −3%) and almost abolished in the PE group (compared with low-risk −63%; CI −77% to −40%; compared with SGA −42%; CI −67% to +1%).

Figure 5:
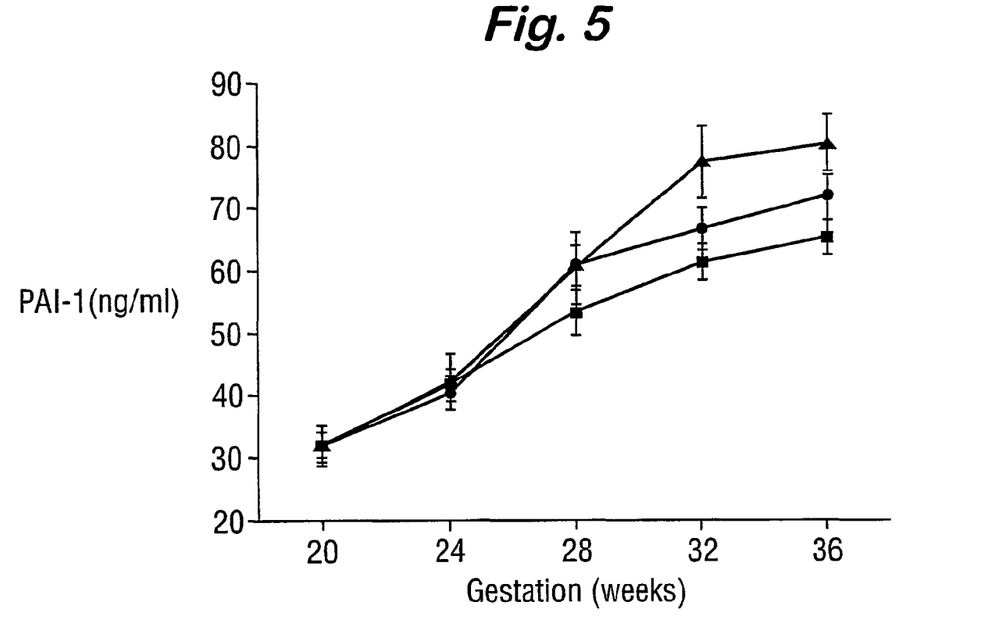
FIG. 5 shows the level of PAI-1 variation during the gestation period, wherein (■) is low risk women, (▲) is women who subsequently developed PE, and (●) is women who did not develop PE but delivered small for gestational age (SGA) infants.
Figure 6:
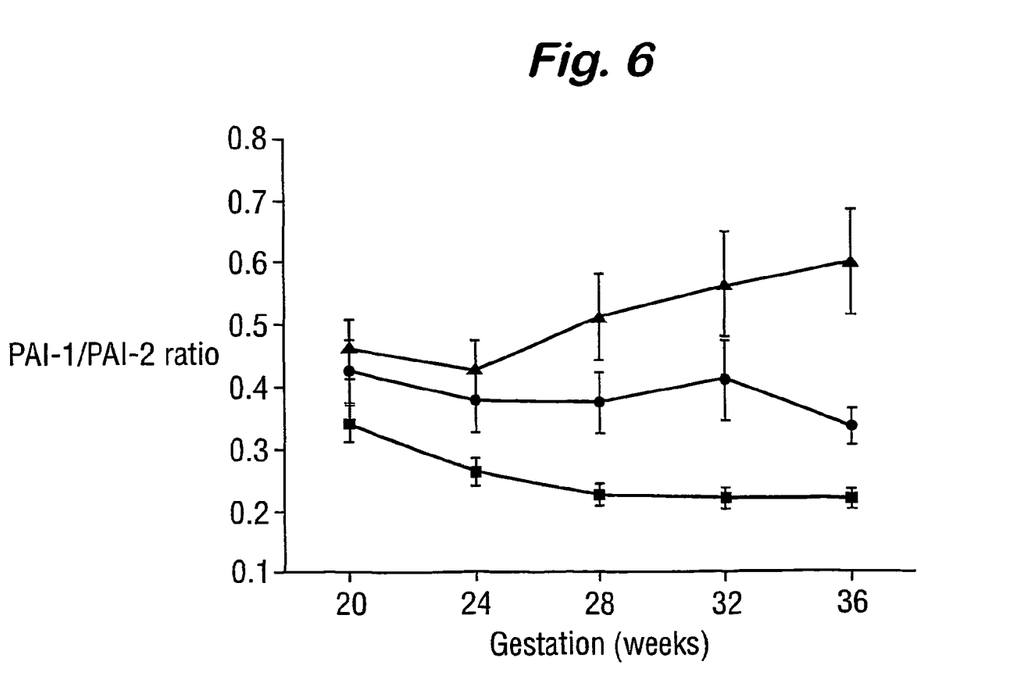
FIG. 6 shows the level of PAI-1/PAI-2 ratio variation during the gestation period, wherein (■) is low risk women, (▲) is women who subsequently developed PE, and (●) is women who did not develop PE but delivered small for gestational age (SGA) infants.

Index of endothelial function and PAI-1/PAI-2 ratio. PAI-1 increased with gestation in all groups. Plasma concentrations were significantly higher in the PE (13%; CI 2% to 25%) compared to low risk group (see FIG. 5). The PAI-1/PAI-2 ratio fell in the low-risk women by −26% (CI −41% to −8%) over gestation, showed no overall change in the SGA group but increased in the PE group by 62% (CI 17% to 122%). Compared with low risk women the PAI-1/PAI-2 ratio was 45% higher in the SGA (CI 15% to 82%) and 85% higher in the PE (CI 44% to 139%) groups, the difference being 28% (CI −3% to 70%) (see FIG. 6).

Lipids Serum triglyceride concentrations increased with gestation, being highest in the PE group (difference from low risk women 29%, CI 2% to 62%). Serum HDL-cholesterol was 13% lower in the PE group than in low risk women (CI −24% to −2%). No differences between groups were observed in total and LDL-cholesterol, apo-A1 or apo-B concentrations (data not shown).

Biochemical Indices and Blood Pressure for Prediction of Pre-eclampsia

Figure 1:
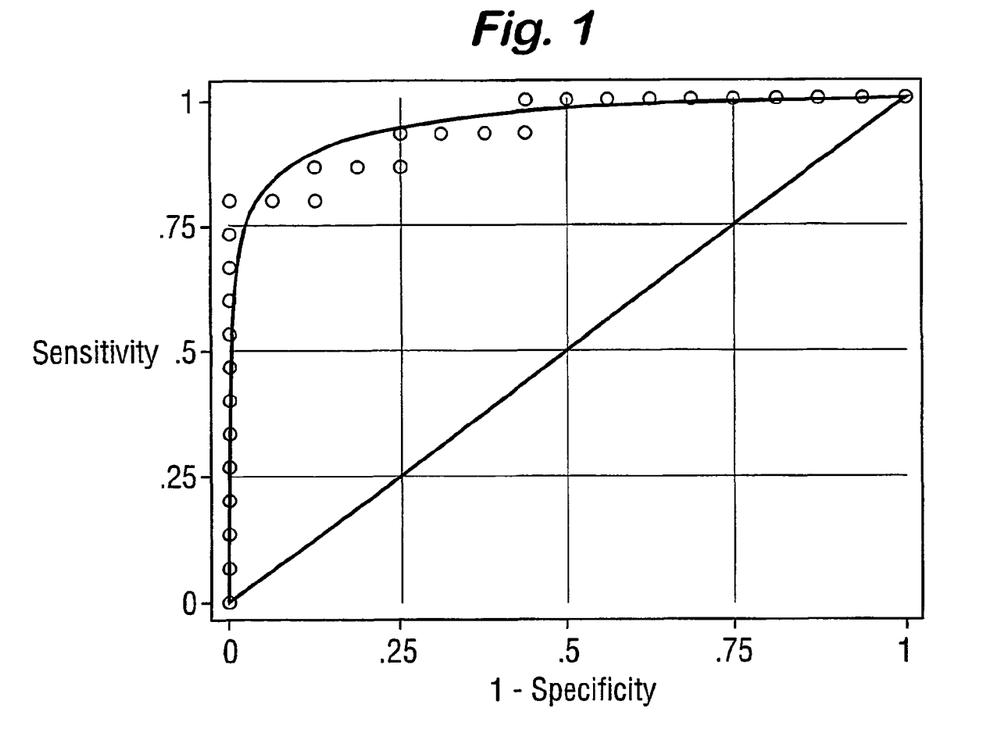
FIG. 1 shows an ROC (Receiver Operation Characteristic) curve for the prediction of PE, based on the formula ($\log_e$[PlGF])−(3.0*{PAI-1/PAI-2 ratio}) from data at 24 weeks' gestation.

Table 9 gives ROC areas for the prediction of PE at 20 and 24 weeks' gestation using six markers identified as potential predictive indicators. At 20 weeks' gestation HDL cholesterol, PAI-1/PAI-2 ratio, leptin and PlGF were able to distinguish PE from low risk women (ROC areas significantly >0.5) and HDL cholesterol and leptin distinguished subsequent PE from SGA. At 24 weeks' gestation, PAI-1/PAI-2 ratio, leptin and PlGF gave ROC values >0.75 (where chance =0.5 and perfect value =1.00) for the PE group compared to low risk, and uric acid was marginally significant. Leptin, PlGF and uric acid distinguished between the PE and SGA groups. A series of logistic regression analyses led to three algorithms with ROC values ≧0.89 for the prediction of PE at 24 weeks and ≧0.80 at 20 weeks (Table 9B) in comparison with the low risk women. These algorithms also distinguished significantly the PE from the SGA group at 24 weeks' gestation. An example of a ROC curve for one of these algorithms ($\log_e$[PlGF])−(3.0*(PAI-1/PAI-2 ratio) at 24 weeks gestation is shown in FIG. 1.

Blood pressure (mean arterial, systolic and diastolic) at booking and at 20 weeks was highly predictive of subsequent PE (e.g., booking blood mean arterial pressure; ROC area % PE vs LR; 0.79, CI 0.66 to 0.92; systolic BP 0.78, CI 0.65 to 0.91 and diastolic BP 0.80, CI 0.68 to 0.98), but these data are strongly influenced by 6 women with pre-existing hypertension in the high risk group, a known risk marker for PE.

There was no statistical evidence that any of the three main indices or any combination was affected by parity, or that values for prediction of PE were different between ethnic groups. Two threshold values chosen to maximise a) sensitivity and b) specificity were defined for each indicator. Values at 24 weeks' gestation, compared to the low risk group are given in Table 10.

Discussion

The data provided herein our knowledge, provides the most comprehensive longitudinal study to date of biochemical indices of the disease in the blood of women destined to develop PE. Previous prospective longitudinal investigations have focussed on evaluation of single biochemical markers, often in fewer subjects and have not compared the profiles in PE with women who delivered small for gestational age infants, but who did not develop PE. The present data, in documenting substantive differences between profiles of the markers in pre-eclamptic pregnancies and those in SGA deliveries uncomplicated by the disease has provided interesting insight into the aetiology of the condition. Additionally combinations of the markers identified, are useful in the prediction of PE. A test that distinguishes subsequent PE from pregnancies characterised by fetal growth restriction alone is clinically useful, particularly as an adjunct to Doppler FVW analysis. Such discrimination early in pregnancy would alert the obstetrician and pregnant woman to heightened surveillance of the symptoms of PE and permit intervention for the prevention of PE should a clinically proven intervention become available e.g. vitamin C and E or calcium supplementation.

Whilst we recognize there are limitations in the use of the birthweight centile as a surrogate marker of fetal growth restriction, important differences from both low risk and PE groups were observed in the SGA group and these have provided valuable mechanistic insight. The majority of high-risk women were recruited on the basis of an abnormal Doppler FVW, indicative of failed trophoblast invasion and high uteroplacental resistance. Plasma concentrations of ascorbic acid in the healthy controls were stable over gestation. In comparison, maternal concentrations of ascorbic acid were significantly low in both SGA and PE groups throughout pregnancy. This would concur with the hypothesis that poor uteroplacental perfusion predisposes to an increase in placental free radical synthesis and, thereby to maternal oxidative stress. Without knowledge of daily intake, a contribution from lower dietary vitamin C cannot be discounted, although the increased rate of consumption of ascorbate documented in the plasma of woman with PE would indicate that excessive metabolic consumption of vitamin C is the more likely explanation. The trend toward elevated concentrations of the isoprostane 8-epi-PGF$_{2\alpha}$ in the PE group (p=O.055), despite considerable scatter in the data, is indicative of oxidative stress. 8-epi-PGF$_{2\alpha}$, a marker of lipid peroxidation, is present in the pre-eclamptic placenta and is variably reported to be increased (Clin. Sci et al., 91: 711-18, 1996) or be normal (Br. J. Obstet. Gynaecol et al., 105: 1195-99, 1998) in the maternal plasma in affected women. Further evidence for oxidative stress lies in the early increase in the PE group, but not in the SGA group of uric acid, a product of the xanthine/xanthine oxidase pathway. Reduced renal clearance of uric acid could also lead to raised plasma concentrations in established PE, but this is unlikely to explain the rise observed prior to clinical manifestation of the disease.

Since ascorbic acid concentrations were low in both PE and SGA groups, a specific role for oxidative stress in the origin of PE might be questioned. However, Hubel et al., pp 453-486, 1999, have suggested that the women who develop PE may be more likely to synthesise damaging lipid peroxides i.e. develop an exaggerated response to the oxidant burden, a theory supported by the much greater trend towards higher values of 8-epi-PGF$_{2\alpha}$ in the PE group. This may arise from the well characterized maternal dyslidipidaemia in PE, including hypertriglyceridaemia (Hubel et al., pp 453-486, 1999) (which occurred as early as 20 weeks' gestation in this study), raised free fatty acid concentrations and decreased LDL particle size which together may contribute to the formation of damaging lipid peroxides and subsequent endothelial cell activation. Other risk markers including diabetes and essential hypertension, with associated microvascular dysfunction, may also influence the circulatory response to a pro-oxidant burden.

The lipid profile in this study showed a specific rise in the serum triglyceride concentration in the women who developed PE. Elevation of triglcyerides has previously been described at 10 weeks gestation in women who later develop PE our study (Hubel et al., pp 453-486, 1999); confirms an early elevation and may suggest that triglycerides play an important pathophysiological role. Previous studies have documented a fall in HDL cholesterol in women with established PE (Hubel et al., pp 453-486, 1999); in the present study HDL was selectively reduced in women who later developed the disease, again implicating dyslipidaemia in the disease process. There was no difference in the LDL cholesterol concentrations, but it is recognized that the properties rather than the absolute concentrations of LDLs are altered in PE.

The abnormal concentration of leptin is likely to reflect placental insufficiency. The substantial increase of maternal blood leptin concentrations in normal pregnancy is generally ascribed to placental synthesis since leptin is synthesised in the placenta (Ashworth et al., 5: 18-24, 2000) although leptin synthesis by maternal adipocytes is likely to contribute. Previous studies have reported a further increase in serum leptin concentrations in women with PE possibly reflecting placental hypoxia (Mise et al., J. Clin. Endocrinol. Metab., 83: 3225-29, 1998). The selective early elevation of leptin concentrations in this study in the women who later developed PE may indicate a role as a prognostic indicator. Early elevation of leptin in women destined to develop PE has recently been described (Anim-Nyame et al., Hum. Reprod., 15: 2003-6, 2000), although no other high risk groups were investigated. Of added interest in the present study was the finding that serum leptin was no different in the healthy pregnant women and those who delivered SGA infants. Correction for BMI (body mass index) did not alter the differences observed. If the rise in leptin in women who developed PE results from hypoxia then this must be presumed to be less pronounced in the SGA group. Alternatively, leptin synthesis is stimulated by cytokines, recognized to contribute to the inflammatory state associated with PE. An increase in the serum leptin concentration may also contribute to an inflammatory response and vascular dysfunction, as the peptide itself has pro-inflammatory properties.

Whereas leptin was selectively increased, another marker of placental insufficiency, PlGF was substantially and selectively reduced in women who later developed PE, also holding promise for this angiogenic marker as a potential predictive indicator. This agrees with previous cross sectional studies reporting that low plasma PlGF concentrations are characteristic of PE (Torry et al., Am. J. Obstet. Gynecol., 179: 1539, 1998) and our study confirms a recent report by Tidwell et al., Am. J. Obstet. Gynecol., 184: 1267-1272, 2001 which has shown an early decrease in plasma PlGF in women who subsequently developed PE. Another report (Livingston et al., Am. J. Obstet. Gynecol., 184: 1218-1220, 2001) in which samples were taken twice, once at 20 weeks and upon diagnosis of PE has shown no difference in PlGF at 20 weeks gestation. In our study the blunted PlGF concentrations whilst markedly more abnormal at 24 weeks gestation were also modestly, but significantly reduced at 20 weeks' gestation. In contrast to leptin, lowered oxygen tension down-regulates PlGF (Ahmed et al., Placenta, 21 S16-24, 2000) and may provide an explanation for failure of the normal increase. The consequences of reduced PlGF may be deleterious, potentially leading to poor trophoblast proliferation, reduced protection against apoptosis and compromised vascular development.

The maternal concentration of PAI-2, also synthesized in placental trophoblast was less selective in discriminating pre-eclamptic pregnancies, being reduced in both the PE and SGA groups, as previously reported (Lindoff et al., Am. J. Obstet. Gynecol., 171: 60-64, 1994). PAI-1, the only endothelial marker studied was elevated, particularly towards the end of pregnancy in the pre-eclamptic group. As PAI-2 falls and PAI-1 increases, as previously reported in established PE (Halligan et al., Br. J. Obstet. Gynaecol., 101: 488-92, 1994), the PAI-1/PAI-2 ratio increases (Reith et al., Br. J. Obstet. Gynaecol., 100: 370-74, 1993). We report here that an abnormally raised PAI-1/PAI-2 ratio also predates the onset of PE.

This study offered the unique opportunity of evaluating the potential value of various combinations of markers in discrimination and prediction of pre-eclamptic pregnancies. No previous study has simultaneously assessed a wide range of relevant biochemical indices. Individually, six of the markers showed significance for prediction of PE at 20 weeks' gestation and serum leptin and HDL cholesterol showed good discrimination between pre-eclamptic and SGA groups. PlGF showed greatest discrimination at 24 weeks. Three specific combinations of the markers studied showed they can be used to predict PE; a combination of PlGF and the PAI-1: PAI-2 ratio, a combination of PAI-2 and PlGF and the combination leptin:PlGF ratio. When measured at 24 weeks these combinations predicted the later development of PE with the potential for high specificity if used as a screening test, and high sensitivity if used in high-risk women. Prediction at 20 weeks was almost as high. These data compare favourably with values for other potential screening tests for PE (Friedman S A et al., and Lindheimer M D. Prediction and Differential Diagnosis in Chesley's Hypertensive Disorders in Pregnancy. Ed: Lindheimer M D, Roberts J M. Cunningham G. Appleton & Lang, Connecticut, USA. pp 201-227, 1999.

Blood pressure was identified as a strong predictor in this study, but the predictive capacity was increased by the inclusion of women with chronic hypertension, a known risk factor for PE.

All the low risk women who volunteered for the study during the course of the clinical trial formed the control group; this had the advantage that the samples from all three groups were similarly treated and stored for an identical period, but led to a significant difference in ethnicity between the pre-eclamptic and low risk groups. We are not aware of any evidence in the literature to suggest any ethnic variation in the markers of oxidative stress, placental or endothelial function studied, although most studies do not consider ethnicity. There was also no evidence from the statistical analysis performed in this study to suggest that ethnicity contributed to any of the differences observed.

In conclusion, the data reports gestational trends in a wide range of markers associated with PE. Our investigation has shown early and selective changes in markers of oxidative stress, lipids and some makers of placental dysfunction suggesting that these may play a role in the aetiology of the disease. Since abnormal profiles were evident several weeks before the clinical onset of PE, we were able to identify combinations of markers that have the potential to identify women who will later develop PE.

All documents cited herein are incorporated by reference.

TABLE 7

Baseline characteristics in low and high-risk women according to clinical outcomes. Low risk women with appropriate for gestational age deliveries (AGA), high risk women who delivered SGA (small for gestational age) infants and high risk women who developed pre-eclampsia (PE).

|  | Low risk AGA | High risk SGA | High risk PE |
| --- | --- | --- | --- |
| N | 27 | 17 | 21 |
| Median Age (years) | 31.9 | 30.8 | 29.9 |
| (IQR) | (30.6-34.1) | (23.8-33.4) | (27.5-34.9) |
| Smokers | 0 | 3 (17%) | 1 (5%) |
| Median body mass index | 23.0 | 22.9 | 27.0 |
| (kg/m$^2$) (IQR) | (21.9-24.9) | (21.5-25.8) | (23.5-32.5) |
| Parity ≧1 | 6 (22%) | 6 (33%) | 15 (71%) |
| 24 week Doppler waveform analysis |  |  |  |
| Median Resistance Index | 0.47 | 0.63 | 0.72 |
| (IQR) | (0.44-0.55) | (0.61-0.69) | (0.62-0.79) |
| Unilateral notch | 0 | 5 (28%) | 3 (14%) |
| Bilateral notch | 0 | 13 (72%) | 18 (86%) |

TABLE 8

Perinatal characteristics in low and high-risk women according to clinical outcomes. Low risk women with appropriate for gestational age deliveries AGA), high risk women who delivered SGA (small for gestational age) infants and high risk women who developed pre-eclampsia (PE),.

|  | Low risk AGA | High risk SGA | High risk PE |
| --- | --- | --- | --- |
| N | 27 | 17 | 21 |
| Median systolic blood pressure; maximum prior to delivery (mmHg) (IQR) | 121 (120-130) | 125 (120-133) | 150 (150-184) |
| Median diastolic blood pressure; maximum prior to delivery (mmHg) (IQR) | 80 (70-82) | 77 (70-86) | 106 (100-118) |

TABLE 8-continued

Perinatal characteristics in low and high-risk women according to clinical outcomes. Low risk women with appropriate for gestational age deliveries AGA), high risk women who delivered SGA (small for gestational age) infants and high risk women who developed pre-eclampsia (PE),.

| | Low risk AGA | High risk SGA | High risk PE |
|---|---|---|---|
| Median maximum urine protein excretion (mg/24 hr) (IQR) | 0 | 0 | 855 (580-3010) |
| Median gestational age at delivery (weeks) (IQR) | 40.3 (39.1-41.2) | 39.7 (38.3-40.6) | 37.1 (34.4-38.6) |
| Median birthweight (grams) (IQR) | 3480 (3340-3770) | 2700 (2353-3015) | 2500 (2070-2940) |
| Median birthweight (centile) (IQR) | 57 (30-82) | 5 (1-7) | 8 (2-24) |
| Small for gestational age infants | 0 | 17 (100%) | 11 (52%) |

TABLE 9a

Prediction of PE using biochemical indices in maternal blood at 20 and 24 week's gestation. ROC areas are given (with 95% confidence intervals). Comparison is made with low risk women with normal outcome (LR) and high risk women who delivered small for gestational age infants (SGA). If confidence intervals do not include 0.5 the difference is significant.

| Biochemical index | 20 weeks' gestation | | 24 week's gestation | |
|---|---|---|---|---|
| | PE vs. LR | PE vs SGA | PE vs. LR | PE vs SGA |
| 8-epi-PGF$_{2\alpha}$ | 0.62 (0.44, 0.81) | 0.53 (0.29, 0.76) | 0.55 (0.35, 0.75) | 0.37 (0.13, 0.61) |
| HDL-cholesterol | 0.73 (0.57, 0.89) | 0.75 (0.57, 0.93) | 0.61 (0.41, 0.82) | 0.64 (0.40, 0.87) |
| Uric acid | 0.57 (0.38, 0.76) | 0.68 (0.48, 0.87) | 0.67 (0.50, 0.85) | 0.70 (0.52, 0.89) |
| PAI-1/PAI-2 ratio | 0.70 (0.52, 0.87) | 0.57 (0.36, 0.78) | 0.76 (0.59, 0.92) | 0.62 (0.42, 0.83) |
| Leptin | 0.71 (0.55, 0.88) | 0.82 (0.67, 0.97) | 0.77 (0.62, 0.92) | 0.88 (0.76, 1.00) |
| Placenta Growth Factor | 0.72 (0.54, 0.91) | 0.60 (0.39, 0.80) | 0.85 (0.71, 0.99) | 0.73 (0.54, 0.92) |

TABLE 9b shows comparison when risk of PE is assessed using combinations of biochemical indices.

| Combination of indices | 20 weeks' gestation | | 24 weeks' gestation | |
|---|---|---|---|---|
| | PE vs. LR | PE vs SGA | PE vs LR | PE vs SGA |
| Log$_e$P1GF-3.0{PAI-1/PAI-2 ratio} | 0.81 (0.65, 0.97) | 0.61 (0.39, 0.83) | 0.95 (0.87, 1.00) | 0.76 (0.57, 0.96) |
| PAI-2 * P1GF | 0.80 (0.63, 0.97) | 0.76 (0.58, 0.94) | 0.89 (0.78, 1.00) | 0.83 (0.68, 0.99) |
| Leptin/P1GF | 0.80 (0.63, 0.97) | 0.76 (0.58, 0.94) | 0.89 (0.78, 1.00) | 0.83 (0.68, 0.99) |

TABLE 10

Sensitivity and specificity (95% Confidence Intervals) for two threshold values calculated from three identified formulae for the prediction of PE.

| Formula | Threshold values | Sensitivity | Specificity |
|---|---|---|---|
| log$_e$[P1GF]–3.0{PAI-1/PAI-2 ratio} | <4.5 | 53% (27%, 79%) | 100% (79%, 100%) |
| | <5 | 80% (52%, 96%) | 88% (62%, 98%) |
| PAI-2 * P1GF | <35 * 10$^3$ | 67% (38%, 88%) | 100% (79%, 100%) |
| | <50 * 10$^3$ | 80% (52%, 96%) | 94% (70%, 100%) |
| leptin/P1GF ratio | >0.1 | 67% (38%, 88%) | 100% (80%, 100%) |
| | >0.05 | 80% (52%, 96%) | 88% (64%, 99%) |

The invention claimed is:

1. A method of predicting whether a pregnant human will subsequently develop pre-eclampsia (PE), comprising:
   determining in a blood sample of the pregnant human a level of placenta growth factor (P1GF) protein and a level of at least one protein or protein ratio selected from the group consisting of:
   i) ratio of plasminogen activator inhibitor-1 (PAI-1) to plasminogen activator inhibitor-2 (PAI-2); and
   ii) leptin; and
   providing a prediction as to whether the pregnant human will subsequently develop PE based on a) the level of P1GF protein and the ratio of PAI-1 protein to PAI-2 protein, or b) the level of P1GF protein and the level of leptin protein.

2. The method according to claim 1, comprising determining the level of P1GF and the ratio of PAI-1/PAI-2 in the sample, wherein a prediction that the pregnant human will subsequently develop PE is given when a reduced level of P1GF is determined in the sample compared to levels in normal pregnant humans and when the ratio of PAI-1 to PAI-2 is determined to be greater than ratios in normal pregnant humans.

3. The method according to claim 1, comprising determining the ratio of leptin to P1GF, wherein a prediction that the pregnant human will subsequently develop PE is given when a ratio of leptin to P1GF in the sample is determined which is greater than the ratio in normal pregnant humans.

4. A method of predicting whether a pregnant human will subsequently develop pre-eclampsia (PE), comprising:
   determining in a blood sample of the pregnant human a level of placenta growth factor (P1GF) protein and a level of plasminogen activator inhibitor-2 (PAI-2) protein, wherein a prediction that the pregnant human will subsequently develop PE is given when combined levels of proteins P1GF and PAI-2 in the sample are less than combined levels found in normal pregnant humans, wherein the levels of proteins P1GF and PAI-2 are combined to form the combined levels using the algorithm:

$$d(\log_e[\text{PAI-2}]) + (\log_e[\text{P1GF}])$$

wherein d is a constant in the range of about 0.03 to 48.6; and providing a prediction as to whether the pregnant human will subsequently develop PE based on the determined combined levels.

5. A method of predicting whether a pregnant human will subsequently develop pre-eclampsia (PE), comprising:

determining in a blood sample of the pregnant human a level of placenta growth factor (P1GF) protein and a level of plasminogen activator inhibitor-2 (PAI-2) protein, wherein a prediction that the pregnant human will subsequently develop PE is given when combined levels of proteins P1GF and PAI-2 in the sample are less than combined levels found in normal pregnant humans, and wherein the level of proteins P1GF and PAI-2 are combined to form the combined levels using the algorithm:

$$[PAI-2]^{d}*[PlGF]$$

wherein d is a constant in the range of about 0.03 to 48.6; and providing a prediction as to whether the pregnant human will subsequently develop PE based on the determined combined levels.

6. A method of predicting whether a pregnant human will subsequently develop pre-eclampsia (PE), comprising:
determining in a blood sample of the pregnant human a level of placenta growth factor (P1GF) protein and a level of plasminogen activator inhibitor-2 (PAI-2) protein, wherein a prediction that the pregnant human will subsequently develop PE is given when combined levels of proteins P1GF and PAI-2 in the sample are less than combined levels found in normal pregnant humans, and wherein the level of proteins P1GF and PAI-2 are combined to form the combined level using the algorithm:

$$[PAI-2]*[PlGF]; \text{ and}$$

providing a prediction as to whether the pregnant human will subsequently develop PE based on the determined combined levels.

7. The method according to claim 2, wherein the level of proteins PlGF and the ratio of PAI-1/PAI-2 are combined using the algorithm:

$$(\log_e[PlGF])-(g*\{PAI-1/PAI-2 \text{ ratio}\})$$

wherein g is a constant in the range of about −19.4 to 3.6.

8. The method according to claim 7, wherein g is 3.0.

9. The method according to claim 1 wherein the sample is obtained from the pregnant human at between 12 and 38 weeks of gestation.

10. The method according to claim 9, wherein the sample is obtained from the pregnant human at between 20 and 36 weeks of gestation.

11. A method of predicting whether a pregnant human will subsequently develop pre-eclampsia (PE), comprising:
determining in a blood sample of the pregnant human a level of placenta growth factor (P1GF) protein and a level of one protein ratio selected from the group consisting of:
(i) the ratio of plasminogen activator inhibitor-1 (PAI-1) to plasminogen activator inhibitor-2 (PAI-2); and
(ii) the ratio of leptin/P1GF; and providing a prediction as to whether the pregnant human will subsequently develop PE based on a) the level of P1GF protein and the PAI-1/PAI-2 protein ratio, or b) the level of P1GF protein and the leptin/P1GF protein ratio.

12. The method according to claim 11, in which a prediction that the pregnant human will subsequently develop PE is given when P1GF in the sample is not increased relative to normal non-pregnant human females and the ratio of PAI-1 to PAI-2 or the ratio of leptin/P1GF in the sample is significantly greater relative to normal pregnant humans.

13. A method of predicting whether a pregnant human will subsequently develop pre-eclampsia (PE), comprising:
determining in a blood sample of the pregnant human a level of placenta growth factor (P1GF) protein and a level of plasminogen activator inhibitor-2 (PAI-2) protein, wherein a prediction that the pregnant human will subsequently develop PE is given when combined levels of proteins P1GF and PAI-2 in the sample are less than combined levels found in normal pregnant humans, and wherein the level of proteins P1GF and PAI-2 are combined to form the combined level using the algorithm:

$$0.75 \,(\log_e PAI-2)+(\log_e P1GF); \text{ and}$$

providing a prediction as to whether the pregnant human will subsequently develop PE based on the determined combined levels.

14. The method according to claim 12, in which the PlGF protein and the ratio PAI-1/PAI-2 protein ratio are determined.

15. The method according to claim 14, in which a prediction that the pregnant human will subsequently develop PE is given when the determined ratio of PAI-1/PAI-2 is greater than the ratio found in normal pregnant humans.

16. The method according to claim 15, further employing the algorithm:

$$(\log_e PlGF)-(3.0 \times \{PAI-1/PAI-2 \text{ ratio}\}).$$

17. The method according to claim 11, in which PlGF and leptin protein levels are determined.

18. The method according to claim 17, in which a prediction that the pregnant human will subsequently develop PE is given when the determined ratio of leptin/P1GF is greater than the ratio found in normal pregnant humans.

19. The method of claim 11 in which the sample is obtained from the pregnant human at 20 weeks of gestation or after.

* * * * *